(12) United States Patent
Ogawa et al.

(10) Patent No.: US 6,252,067 B1
(45) Date of Patent: Jun. 26, 2001

(54) METHOD OF PREPARING OXOQUAZEPAM

(75) Inventors: Masaki Ogawa; Fumio Kita, both of Yachiyo (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 09/410,031

(22) Filed: Oct. 1, 1999

(30) Foreign Application Priority Data

Dec. 14, 1998 (JP) .................................................. 10-354395

(51) Int. Cl.$^7$ ................................................ C07D 243/26

(52) U.S. Cl. ............................................................ 540/504

(58) Field of Search .............................................. 540/504

(56) References Cited

U.S. PATENT DOCUMENTS 5,658,901 * 8/1997 Caremon et al. .................... 514/221

FOREIGN PATENT DOCUMENTS

1179124 * 1/1970 (GB) .
2065112 * 6/1981 (GB) .
2065112A * 6/1999 (GB) .

OTHER PUBLICATIONS

"Webster's New World Dictionary, College Ed." no author listed, World Publishing, 1962.*

Lowry, Thomas H. and Richardson, Kathleen, "Mechanism and Theory in Organic Chemistry, 3rd. Ed.", Harper & Row, New York, 1987.*

P. Johnstrom et al., J. Labelled Compd. & Radiopharm., 36 (1995), 537–548.*

Morrison et al., Organic Chemistry, IV Edition, pp. 204–211, 1983.*

Johnstrom, P. and Stone–Elander, S., J. labelled Comp. Radiopharm., 26, 1995, p 537–546.*

J. March, Advanced Organic Chemistry, pps. 310–316, "Aliphatic Nucleophilic Subsitution," 1985.

* cited by examiner

*Primary Examiner*—Mark L Berch
*Assistant Examiner*—Thomas C McKenzie
(74) *Attorney, Agent, or Firm*—Oblon, Spivak, McClelland, Maier & Neustadt, P.C.

(57) ABSTRACT

A method of preparing oxoquazepam which comprises reacting 2,2,2-trifluoroethyl trifluoromethanesulfonate with 7-chloro-1,3-dihydro-5-(2-fluorophenyl)-2H-1,4-benzodiazepin-2-one in tetrahydrofuran or ethyl acetate in the presence of potassium carbonate under reflux. According to the method of the present invention, high purity oxoquazepam can be manufactured in high yields.

8 Claims, No Drawings

METHOD OF PREPARING OXOQUAZEPAM

BACKGROUND OF THE INVENTION

1. Field of the Invention

The present invention relates to a method of preparing oxoquazepam which is an intermediate material for quazepam shown by the following formula (3) which is important in medicines such as sedatives.

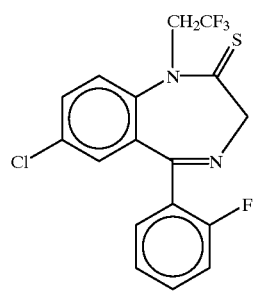

(3)

2. Description of the Background

Oxoquazepam is considered to be prepared by the trifluoroethylation of 7-chloro-1,3-dihydro-5-(2-fluorophenyl)-2H-1,4-benzodiazepin-2-one as shown by the following formula.

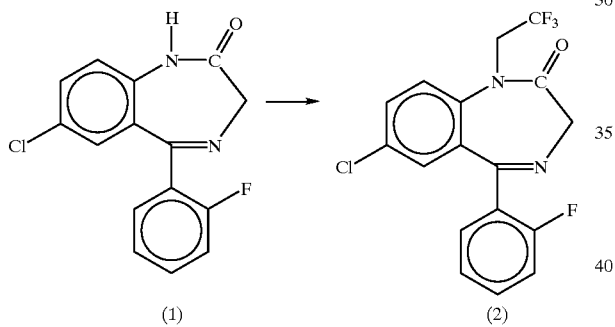

However, trifluoroethylation of this compound does not proceed due to the strong attraction to electrons of a fluorine atom when using conventional halides such as 2,2,2-trifluoroethyl iodide.

Perfluoroalkylsulfonate which possesses higher reactivity, specifically, 2,2,2-trifluoroethyl perfluoro-n-butanesulfonate has been found as a trifluoroethylation agent instead of such conventional halides (Japanese Patent Publication No. 60663/1990).

However, 2,2,2-trifluoroethyl perfluoro-n-butanesulfonate used as the trifluoroethylation agent is a special compound which cannot be produced on an industrial level and is expensive.

The use of anhydrous polar neutral solvents such as dimethylformamide, dimethylsulfoxide, dimethylacetamide, sulfolane, or mixed solvents of these solvents with other solvents such as hydrocarbons (for example, benzene or toluene), halogenated hydrocarbons (for example, methylene dichloride or chloroform), and ethers (for example, diethyl ether or dioxane) has been disclosed as an effective method of the trifluoroethylation reaction using 2,2,2-trifluoroethyl perfluoro-n-butanesulfonate (Japanese Patent Publication No. 24807/1990). Such a solvent is used to promote N-alkylation reaction in the reaction involving a compound containing both an amine and a carbonyl group, because the ratio of N-alkylation to O-alkylation is controlled by the polarity of a reaction medium in such a reaction.

Oxoquazepam used as an intermediate material for medicines must include only a small amount of impurities, in particular, only a small amount of analogous materials. Therefore, a method of preparing high purity oxoquazepam with a high yield has been demanded.

Accordingly, an object of the present invention is to provide a method of preparing high purity oxoquazepam with a high yield using a trifluoroethylation agent which is readily available and cheap.

In view of the above-described situation, the present inventors have conducted extensive studies. As a result, the present inventors have found that high purity oxoquazepam can be prepared at high yield by the trifluoroethylation of 7-chloro-1,3-dihydro-5-(2-fluorophenyl)-2H-1,4-benzodiazepin-2-one using commercially available 2,2,2-trifluoroethyl trifluoromethanesulfonate (J. Org. Chem. 30, 4322. (1965)) as a trifluoroethylation agent in tetrahydrofuran or ethyl acetate as a solvent in the presence of potassium carbonate under reflux. This finding has led to the completion of the present invention.

SUMMARY OF THE INVENTION

Specifically, an object of the present invention is to provide a method of preparing oxoquazepam shown by the following formula (2),

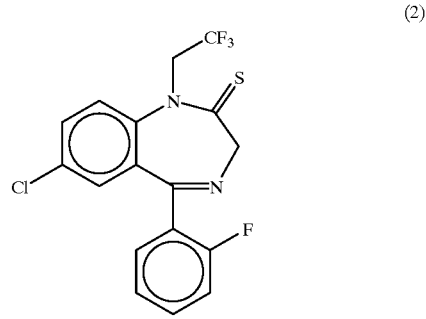

(2)

which comprises reacting 2,2,2-trifluoroethyl trifluoromethanesulfonate with 7-chloro-1,3-dihydro-5-(2-fluorophenyl)-2H-1,4-benzodiazepin-2-one shown by the following formula (1) in tetrahydrofuran or ethyl acetate in the presence of potassium carbonate under reflux.

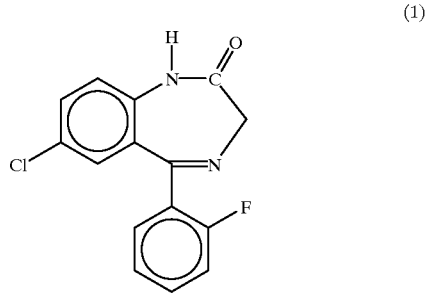

(1)

Other objects, features and advantages of the invention will hereinafter become more readily apparent from the following description.

DETAILED DESCRIPTION OF THE PREFERRED EMBODIMENTS

The amount of 2,2,2-trifluoroethyl trifluoromethanesulfonate used in the present invention is preferably equimolar with or slightly more than the amount of the compound (1) in a molar ratio. The amount of 1.15–1.2 times mol of the compound (1) is sufficient.

The amount of potassium carbonate used in the present invention is preferably more than 2,2,2-trifluoroethyl trifluoromethanesulfonate in a molar ratio, in particular, about 1.5–3 times mol of 2,2,2-trifluoroethyl trifluoromethanesulfonate.

In the present invention, ethyl acetate or tetrahydrofuran is used as a solvent. If a solvent having a polarity higher than that of these compounds such as acetone, acetonitrile, or dimethylformamide is used, O-alkylates are produced at about a 30% yield. If a solvent having a polarity lower than that of these compounds such as toluene is used, the reaction scarcely proceeds and the raw materials are left unreacted. It is preferable to use ethyl acetate or tetrahydrofuran in an amount so that the polarity of the solvent is not affected by the polarity of the solute, specifically, 5 times or more of 7-chloro-1,3-dihydro-5-(2-fluorophenyl)-2H-1,4-benzodiazepin-2-one.

According to the method of the present invention using ethyl acetate or tetrahydrofuran, the raw materials disappear after being refluxed for 8–20 hours to obtain an N-alkylate, specifically, oxoquazepam. The ratio of the resulting by-product O-alkylates is 3% or less.

After the reaction, potassium carbonate is removed and the reactant is crystallized from a saturated hydrocarbon solvent to obtain high purity oxoquazepam.

According to the method of the present invention, high purity oxoquazepam can be manufactured at high yield at a low cost.

EXAMPLES

The present invention will be described in detail by examples, which should not be construed as limiting the present invention.

Example 1

1 g of 7-chloro-1,3-dihydro-5-(2-fluorophenyl)-2H-1,4-benzodiazepin-2-one, 0.94 g of 2,2,2-trifluoroethyl trifluoromethanesulfonate, and 1 g of potassium carbonate were added to 10 ml of ethyl acetate, and the mixture was refluxed for 16 hours. After cooling, 10 ml of water was added to wash the reactant. The ethyl acetate layer was separated and then concentrated under vacuum. Hexane was added to the residue and the precipitated crystal was filtered to obtain 1.18 g of oxoquazepam (yield: 92%).

Example 2

2 g of 7-chloro-1,3-dihydro-5-(2-fluorophenyl)-2H-1,4-benzodiazepin-2-one, 2 g of 2,2,2-trifluoroethyl trifluoromethanesulfonate, and 2 g of potassium carbonate were added to 20 ml of tetrahydrofuran, and the mixture was refluxed for 20 hours. After cooling, the reactant was filtered. The filtrate was concentrated under vacuum. Hexane was added to the residue and the precipitated crystal was filtered to obtain 2.45 g of oxoquazepam (yield: 95%).

Obviously, numerous modifications and variations of the present invention are possible in light of the above teachings. It is therefore to be understood that, within the scope of the appended claims, the invention may be practiced otherwise than as specifically described herein.

What is claimed is:

1. A method of preparing oxoquazepam having the following formula (2),

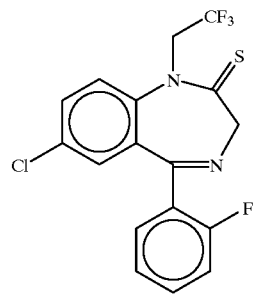

(2)

which comprises reacting 2,2,2-trifluoroethyl trifluoromethanesulfonate with 7-chloro-1,3-dihydro-5-(2-fluorophenyl)-2H-1,4-benzodiazepin-2-one having the following formula (1) in tetrahydrofuran or ethyl acetate in the presence of potassium carbonate under reflux.

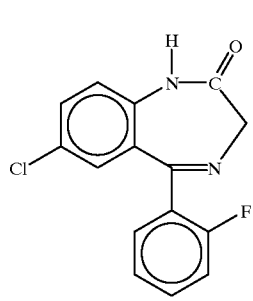

(1)

2. The method of claim 1, wherein the amount of potassium carbonate used is about 1.5 to 3 molar times that of 2,2,2,-trifluoroethyl trifluoromethanesulfonate.

3. The method of claim 1, wherein said reaction is conducted under reflux for 8 to 20 hours.

4. The method of claim 1, wherein a ratio of by-product O-alkylate produced is 3% or less.

5. The method of claim 1, wherein a yield of oxoquazepam of at least 92% is obtained.

6. The method of claim 1, wherein a yield of oxoquazepam of 95% is obtained.

7. The method of claim 1, which further comprises crystallizing the oxoquazepam produced by addition of hexane thereto.

8. The method of claim 1, wherein an amount of ethyl acetate or tetrahydrofuran is used which is five times or more than said 7-chloro-1,3-dihydro-5-(2-fluorophenyl)-2H-1,4-benzodiazepin-2-one.

* * * * *